United States Patent
Hone et al.

(10) Patent No.: US 9,617,219 B2
(45) Date of Patent: Apr. 11, 2017

(54) POLYMORPHS OF 3-DIFLUOROMETHYL-1-METHYL-1 H-PYRAZOLE-4-CARBOXYLIC ACID (9-DICHLORO-METHYLENE-1,2,3,4-TETRAHYDRO-1,4-METHANO-NAPHTHALEN-5-YL)-AMIDE

(71) Applicant: Syngenta Participations AG, Basel (CH)

(72) Inventors: John Hone, Bracknell Berkshire (GB); Ian Kevin Jones, Bracknell Berkshire (GB); Neil George, Bracknell Berkshire (GB)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/121,081

(22) PCT Filed: Feb. 24, 2015

(86) PCT No.: PCT/EP2015/053828
§ 371 (c)(1),
(2) Date: Aug. 24, 2016

(87) PCT Pub. No.: WO2015/128322
PCT Pub. Date: Sep. 3, 2012

(65) Prior Publication Data
US 2016/0362379 A1    Dec. 15, 2016

(30) Foreign Application Priority Data
Feb. 27, 2014    (GB) .................................. 1403438.3

(51) Int. Cl.
*C07D 231/14*    (2006.01)
*A01N 45/02*    (2006.01)

(52) U.S. Cl.
CPC ........... *C07D 231/14* (2013.01); *A01N 45/02* (2013.01); *C07B 2200/13* (2013.01)

(58) Field of Classification Search
None
See application file for complete search history.

(56) References Cited

U.S. PATENT DOCUMENTS 8,524,915 B2 *    9/2013    Schleth ............... C07C 17/2635
548/374.1
2012/0136162 A1    5/2012    Gribkov et al.

FOREIGN PATENT DOCUMENTS

| WO | 2008/131901 A1 | 11/2008 |
| WO | 2011/131544 A1 | 10/2011 |
| WO | 2011/131545 A1 | 10/2011 |
| WO | 2011/131546 A1 | 10/2011 |

OTHER PUBLICATIONS

International Search Report and Written Opinion mailed Apr. 21, 2015 for International Patent Application No. PCT/EP2015/053828.

* cited by examiner

*Primary Examiner* — Kamal Saeed
(74) *Attorney, Agent, or Firm* — R. Kody Jones (57) ABSTRACT

The present invention relates to solid forms of the fungicide of formula (I): compositions comprising the solid forms and methods of their use as fungicides.

8 Claims, 7 Drawing Sheets

POLYMORPHS OF 3-DIFLUOROMETHYL-1-METHYL-1 H-PYRAZOLE-4-CARBOXYLIC ACID (9-DICHLORO-METHYLENE-1,2,3,4-TETRAHYDRO-1,4-METHANO-NAPHTHALEN-5-YL)-AMIDE

RELATED APPLICATION INFORMATION

This application is a 371 of International Application No. PCT/EP 2015/053828, filed 24 Feb. 2015, which claims priority to GB Patent Application No. 1403438.3, filed 27 Feb. 2014, the contents of which are incorporated herein by reference.

This invention relates to solid forms of heterocyclic amide derivatives, compositions comprising the solid forms and methods of their use as safeners.

WO 2007/048556 discloses that certain heterocyclic amide derivatives have microbicidal activity, in particular, fungicidal activity. In particular, a compound of formula I, 3-difluoromethyl-1-methyl-1H-pyrazole-4-carboxylic acid (9-dichloromethylene-1,2,3,4-tetrahydro-1,4-methano-naphthalen-5-yl)-amide is disclosed:

(I)

New solid forms of this compound, their compositions and methods of their preparation and use have now been discovered.

Accordingly, the present invention relates to novel crystalline forms of a heterocyclic amide derivative of formula I:

(I)

The crystalline polymorph of the invention may be characterised by the unit cell parameters of its single crystal as shown in Table 1. The polymorph was obtained using the method of Example 1.

TABLE 1

| Class | Orthorhombic |
|---|---|
| Space Group | P n a $2_1$ |
| Cell Lengths (Å) | a = 18.28(5) |
| | b = 12.65(5) |
| | c = 7.81(5) |
| Cell Angles (°) | α = 90.00 |
| | β = 90.00 |
| | γ = 90.00 |
| Unit Cell Volume (Å$^3$) | 1805.0(5) |
| Z | 4 |

In the table, a, b, c=Length of the edges of the unit cell; α, β, γ=Angles of the unit cell; and Z=molecules per cell.

Thus, in one embodiment of the present invention, the crystalline polymorph of the invention has the following lattice parameters: a=18.28(5), b=12.65(5), c=7.81(5), α=90.00, β=90.00, γ=90.00 and volume=1805.0(5) Å$^3$.

The crystalline polymorph may also be characterised by a powder X-ray diffraction pattern expressed in terms of 2θ angles or d spacings. Thus, in another embodiment of the invention, the crystalline polymorph of the invention has a powder X-ray diffraction pattern comprising at least three, at least six, at least nine, at least twelve, at least fifteen or all d spacing values selected from the group consisting of 10.45±0.2, 7.45±0.2, 6.71±0.2, 6.31±0.2, 5.99±0.2, 5.42±0.2, 5.23±0.2, 4.78±0.2, 4.60±0.2, 4.53±0.2, 4.33±0.2, 4.14±0.2, 3.97±0.2, 3.86±0.2, 3.73±0.2, 3.62±0.2, 3.49±0.2, 3.37±0.2, 3.30±0.2, 3.23±0.2, 3.19±0.2, 3.14±0.2, 3.06±0.2 and 3.00±0.2. These d spacing values are derived from a powder X-ray diffraction pattern of the polymorph obtained using the method of Example 1. The values are generated using an average wavelength of 1.54184 Å with a 2θ step size of 0.02°. In addition, the crystalline polymorph is also characterised by the absence of a d spacing value at 16.58±0.2 and at 16.84±0.2, peaks found in the anhydrous form Form 1 and Form 2 polymorphs, respectively, of the compound of formula I detailed below.

The crystalline polymorph of the invention has been found to be a monohydrate containing 4.3±0.2% w/w water. Thus, in a further embodiment of the invention there is provided a crystalline polymorph of the compound of formula I, which is a monohydrate containing 4.3±0.2% w/w water.

In another embodiment, the crystalline polymorph of the invention has a dehydration/melting point of between 80 and 125° C. This melting point is obtained using Differential Scanning calorimetry (DSC) with a heating rate of 10° C./minute.

A further polymorph of the compound of formula (I) has also been identified—an anhydrous form (anhydrous Form 1), which has a melting point of 149° C.±5° C. This polymorph was obtained using the method of Example 2. This polymorph may also be characterised by the unit cell parameters of its single crystal as shown in Table 2.

TABLE 2

| Class | Orthorhombic |
|---|---|
| Space Group | Pbca |
| Cell Lengths (Å) | a = 13.43(5) |
| | b = 8.16(5) |
| | c = 33.15(5) |
| Cell Angles (°) | α = 90.00 |
| | β = 90.00 |
| | γ = 90.00 |
| Unit Cell Volume (Å$^3$) | 3633.6(5) |
| Z | 8 |

In the table, a, b, c=Length of the edges of the unit cell; α, β, γ=Angles of the unit cell; and Z=molecules per cell.

Thus, the anhydrous polymorph has the following lattice parameters: a=13.43(5), b=8.16(5), c=33.15(5), α=90.00, β=90.00, γ=90.00 and volume=3633.6(5) Å$^3$.

This crystalline polymorph may also be characterised by a powder X-ray diffraction pattern expressed in terms of 2θ angles or d spacings. Thus, in another embodiment of the invention, the anhydrous Form 1 crystalline polymorph of the invention has a powder X-ray diffraction pattern comprising at least three, at least six, at least nine, at least twelve, at least fifteen or all d spacing values selected from the group consisting of 16.58±0.2, 10.43±0.2, 6.82±0.2, 6.71±0.2, 6.43±0.2, 6.22±0.2, 5.52±0.2, 5.34±0.2, 5.19±0.2, 5.12±0.2, 4.95±0.2, 4.69±0.2, 4.40±0.2, 4.32±0.2, 4.27±0.2, 4.08±0.2, 3.96±0.2, 3.83±0.2, 3.53±0.2, 3.47±0.2, 3.38±0.2, 3.33±0.2, 3.29±0.2, 3.11±0.2, 3.05±0.2 and 3.00±0.2. These d spacing values are derived from a powder X-ray diffraction pattern of the polymorph that has been calculated using data from the unit cell of the single crystal. The values are generated using an average wavelength of 1.54184 Å with a 2θ step size of 0.02°.

A still further polymorph of the compound of formula (I) has also been identified—a second metastable anhydrous form (anhydrous Form 2), which has a melting point of 147° C.±5° C. This polymorph was obtained using the method of Example 2.

This crystalline polymorph may be characterised by a powder X-ray diffraction pattern expressed in terms of 2θ angles or d spacings. Thus, in another embodiment of the invention, the anhydrous Form 2 crystalline polymorph of the invention has a powder X-ray diffraction pattern comprising at least three, at least six, at least nine, at least twelve, at least fifteen or all d spacing values selected from the group consisting of 16.84±0.2, 10.27±0.2, 7.71±0.2, 6.76±0.2, 6.54±0.2, 5.95±0.2, 5.61±0.2, 5.25±0.2, 5.10±0.2, 4.99±0.2, 4.45±0.2, 4.37±0.2, 4.15±0.2, 3.88±0.2, 3.74±0.2, 3.66±0.2, 3.58±0.2, 3.43±0.2, 3.37±0.2 and 3.28±0.2. These d spacing values are derived from a powder X-ray diffraction pattern of the polymorph obtained using the method of Example 2. The values are generated using an average wavelength of 1.54184 Å with a 2θ step size of 0.02°.

In the context of the present invention, a polymorph is a particular crystal form of a chemical compound that can exist in more than one crystal form in the solid state. A crystal form of a compound contains the constituent molecules arranged in orderly repeating patterns extending in all three spatial dimensions (in contrast, an amorphous solid form has no long-range order in the position of molecules). Different polymorphs of a compound have different arrangements of atoms and or molecules in their crystal structure. When the compound is a biologically active compound, such as a fungicide, the difference in crystal structures can lead to different polymorphs having differing chemical, physical and biological properties. Properties which may be affected include crystal shape, density, hardness, colour, chemical stability, melting point, hydroscopicity, suspensibility, dissolution rate and biological availability. As such, a specific polymorph may have properties which make it more advantageous in a particular use relative to another polymorph of the same compound: in particular, the physical, chemical and biological properties listed above can have a significant effect on the development of production methods and formulations and the quality and efficacy of plant treatment agents, such as fungicides. It is noted that predicting whether the solid state of a compound may be present as more than one polymorph is not possible and nor is it possible to predict the properties of any of these crystal forms.

In particular, use of a specific polymorph may allow use of new formulations compared with existing polymorphic/amorphous forms of a compound. This might be advantageous for a number of reasons. For example, a suspension concentrate (SC) formulation may be preferred over an emulsion concentrate (EC) because the lack of solvent in the SC often means that the formulation is likely to be less phytotoxic than an equivalent EC formulation—however, if the existing form of a compound is not stable in such an SC formulations, polymorphic conversion might occur leading to unwanted crystal growth. Such crystal growth is detrimental because it leads to, for example, thickening and potentially solidification of the formulation which can lead to blockages in application equipment, e.g. in spray nozzles in agricultural application machinery. Using a stable polymorphic form would overcome these issues.

Assaying the solid phase for the presence of crystals may be carried out by conventional methods known in the art. For example, it is convenient and routine to use powder X-ray diffraction techniques. Other techniques which may be used include differential scanning calorimetry (DSC), thermogravimetric analysis (TGA) and Raman or Infra-red spectroscopy, NMR, gas chromatography or HPLC. Single crystal X-ray diffraction is especially useful in identifying crystal structures.

The polymorphs of the invention may be applied in unchanged form but are more preferably incorporated into agrochemical compositions by conventional means. Accordingly, in a further aspect, the invention provides an agrochemical composition comprising a polymorph of the invention as defined above and at least one an agriculturally acceptable carrier or diluent.

The agrochemical compositions comprising the polymorphs of the present invention can be used for the control of plant pathogenic fungi on a number of plant species. Accordingly, the invention also provides a method of preventing or controlling fungal infection on plants or plant propagation material comprising treating the plant or plant propagation material with a fungicidally effective amount of an agricultural composition of the invention. By 'plant propagation material' is meant seeds of all kinds (fruit, tubers, bulbs, grains etc.), cuttings, cut shoots and the like.

In particular, the agrochemical compositions of the invention can be used to control, for example, phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

The agrochemical compositions of the present invention are suitable for controlling such disease on a number of plants and their propagation material including, but not limited to the following target crops: cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutata* Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia Willd.*), St. Augustinegrass (*Stenotaphrum secundatum* (Walt.) Kuntze); and centipedegrass (*Eremochloa ophiuroides* (Munro.) Hack.)).

In addition 'crops' are to be understood to include those crops that have been made tolerant to pests and pesticides, including herbicides or classes of herbicides, as a result of conventional methods of breeding or genetic engineering. Tolerance to e.g. herbicides means a reduced susceptibility to damage caused by a particular herbicide compared to conventional crop breeds. Crops can be modified or bred so as to be tolerant, for example, to HPPD inhibitors such as mesotrione or EPSPS inhibitors such as glyphosate.

In particular, the compositions according to the invention are particularly effective against powdery mildews; rusts; leafspot species; early blights and molds; especially against *Septoria*, *Puccinia*, *Erysiphe*, *Pyrenophora* and *Tapesia* in cereals; *Phakopsora* in soybeans; *Hemileia* in coffee; *Phragmidium* in roses; *Alternaria* in potatoes, tomatoes and cucurbits; *Sclerotinia* in turf, vegetables, sunflower and oil seed rape; black rot, red fire, powdery mildew, grey mold and dead arm disease in vine; *Botrytis cinerea* in fruits; *Monilinia* spp. in fruits and *Penicillium* spp. in fruits.

The compositions according to the invention are furthermore particularly effective against seedborne and soilborne diseases, such as *Alternaria* spp., *Ascochyta* spp., *Botrytis cinerea*, *Cercospora* spp., *Claviceps purpurea*, *Cochliobolus sativus*, *Colletotrichum* spp., *Epicoccum* spp., *Fusarium graminearum*, *Fusarium moniliforme*, *Fusarium oxysporum*, *Fusarium proliferatum*, *Fusarium solani*, *Fusarium subglutinans*, *Gäumannomyces graminis*, *Helminthosporium* spp., *Microdochium nivale*, *Phoma* spp., *Pyrenophora graminea*, *Pyricularia oryzae*, *Rhizoctonia solani*, *Rhizoctonia cerealis*, *Sclerotinia* spp., *Septoria* spp., *Sphacelotheca reilliana*, *Tilletia* spp., *Typhula incarnata*, *Urocystis occulta*, *Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The compositions according to the invention are furthermore particularly effective against post harvest diseases such as *Botrytis cinerea*, *Colletotrichum musae*, *Curvularia lunata*, *Fusarium semitecum*, *Geotrichum candidum*, *Monilinia fructicola*, *Monilinia fructigena*, *Monilinia laxa*, *Mucor piriformis*, *Penicilium italicum*, *Penicilium solitum*, *Penicillium digitatum* or *Penicillium expansum* in particular against pathogens of fruits, such as pomefruits, for example apples and pears, stone fruits, for example peaches and plums, citrus, melons, papaya, kiwi, mango, berries, for example strawberries, avocados, pomegranates and bananas, and nuts.

The compositions according to the invention are particularly useful for controlling the following diseases on the following crops:

*Alternaria* species in fruit and vegetables; *Ascochyta* species in pulse crops; *Botrytis cinerea* in strawberries, tomatoes, sunflower, pulse crops, vegetables and grapes, such as *Botrytis cinerea* on grape; *Cercospora arachidicola* in peanuts; *Cochliobolus sativus* in cereals; *Colletotrichum* species in pulse crops; *Erysiphe* species in cereals; such as *Erysiphe graminis* on wheat and *Erysiphe graminis* on barley; *Erysiphe cichoracearum* and *Sphaerotheca fuliginea* in cucurbits; *Fusarium* species in cereals and maize; *Gäumannomyces graminis* in cereals and lawns; *Helminthosporium* species in maize, rice and potatoes; *Hemileia vastatrix* on coffee; *Microdochium* species in wheat and rye; *Mycosphaerella fijiensis* in banana; *Phakopsora* species in soybeans, such as *Phakopsora pachyrizi* in soybeans; *Puccinia* species in cereals, broadleaf crops and perennial plants; such as *Puccinia recondita* on wheat, *Puccinia striiformis* on wheat and *Puccinia recondita* on barley; *Pseudocercosporella* species in cereals, such as *Pseudocercosporella herpotrichoides* in wheat; *Phragmidium mucronatum* in roses; *Podosphaera* species in fruits; *Pyrenophora* species in barley, such as *Pyrenophora teres* on barley; *Pyricularia oryzae* in rice; *Ramularia collo-cygni* in barley; *Rhizoctonia* species in cotton, soybean, cereals, maize, potatoes, rice and lawns, such as *Rhizoctonia solani* on potato, rice, turf and cotton; *Rhynchosporium secalis* on barley, *Rhynchosporium secalis* on rye; *Sclerotinia* species in lawns, lettuce, vegetables and oil seed rape, such as *Sclerotinia sclerotiorum* on oilseed rape and *Sclerotinia homeocarpa* on turf; *Septoria* species in cereals, soybean and vegetables, such as *Septoria tritici* on wheat, *Septoria nodorum* on wheat and *Septoria glycines* on soybean; *Sphacelotheca reilliana* in maize; *Tilletia* species in cereals; *Uncinula necator*, *Guignardia bidwellii* and *Phomopsis viticola* in vines; *Urocystis occulta* in rye; *Uromyces* species in beans; *Ustilago* species in cereals and maize; *Venturia* species in fruits, such as *Venturia inequalis* on apple; *Monilinia* species on fruits; *Penicillium* species on citrus and apples.

The rate at which the agrochemical composition of the invention is applied will depend upon the particular type of fungus to be controlled, the degree of control required and the timing and method of application and can be readily determined by the person skilled in the art. In general, the compositions of the invention can be applied at an application rate of between 0.005 kilograms/hectare (kg/ha) and about 5.0 kg/ha, based on the total amount of active fungicide in the composition. An application rate of between about 0.1 kg/ha and about 1.5 kg/ha is preferred, with an application rate of between about 0.3 kg/ha and 0.8 kg/ha being especially preferred.

In practice, the agrochemical compositions comprising the polymorphs of the invention are applied as a formulation containing the various adjuvants and carriers known to or used in the industry. They may thus be formulated as granules, as wettable powders, as emulsifiable concentrates, as suspension concentrates (including oil dispersions), as powders or dusts, as flowables, as solutions, as suspensions or emulsions, suspo-emulsions or as controlled release forms such as microcapsules. Suitably, the agrochemical composition of the invention may be formulated as a suspension concentrate, a suspo-emulsion an emulsion concentrate or a wet granulation. These formulations are described in more detail below and may contain as little as about 0.5% to as much as about 95% or more by weight of the active ingredient in the form of the polymorph. The optimum amount will depend on formulation, application equipment and nature of the plant pathogenic fungi to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain by weight about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient by weight may range from about 0.5% to about 95% of the concentrate.

Suspension concentrates are formulations in which finely divided solid particles of the active compound are stably suspended. The solid particles may be suspended in an aqueous solution or in an oil (as an oil dispersion). Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient by weight may range from about 0.5% to about 95% of the concentrate.

Granular formulations include both extrudates and relatively coarse particles and may be applied without dilution to the area in which control of plant pathogenic fungi is required or dispersed in a spray tank before application, for example. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations for use without dilution normally contain by weight about 5% to about 25% active ingredients which may include surface-active agents such as heavy aromatic naphthas, kerosene and other petroleum fractions, or vegetable oils; and/or stickers such as dextrins, glue or synthetic resins. When the granules are to be dispersed in a spray tank before application, the active ingredient content by weight may be increased up to 80%.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically from about 1 to about 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre (and preferably from 1 to 2 millimetres) in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of the formulations described above include wetting, dispersing or emulsifying agents. Examples are alkyl and alkylaryl sulphonates and sulphates and their salts, polyhydric alcohols; polyethoxylated alcohols, esters and fatty amines. These agents, when used, normally comprise from 0.1% to 40% by weight of the formulation.

Suitable agricultural adjuvants and carriers that are useful in formulating the compositions of the invention in the formulation types described above are well known to those skilled in the art. Suitable examples of the different classes are found in the non-limiting list below.

Liquid carriers that can be employed include water and any solvents in which the polymorph has no or limited solubility e.g. toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulphonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulphates, such as diethanolammonium lauryl sulphate; alkylarylsulphonate salts, such as calcium dodecylbenzenesulphonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulphonate salts, such as sodium dibutylnaphthalenesulphonate; dialkyl esters of sulphosuccinate salts, such as sodium di(2-ethylhexyl) sulphosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like.

Each of the above formulations can be prepared as a package containing the fungicides together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots. The formulations of the invention may also be used for dressing applications on plant propagation material to provide protection against fungus infections on the plant propagation material as well as against phytopathogenic fungi occurring in the soil. Suitably, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of plant cuttings or twigs serving propagation.

Suitably, the agrochemical compositions and formulations of the present invention are applied prior to disease development. Rates and frequency of use of the formulations are those conventionally used in the art and will depend on the risk of infestation by the fungal pathogen.

The compositions and formulations of the present invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth form yet further aspects of the invention.

When a polymorph of the invention is combined with at least one additional fungicide, the following mixtures of the polymorph are preferred: mixtures with acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, berberine, bethoxazin, biloxazol, binapacryl, biphenyl, bitertanol, bithionol, bixafen, blasticidin-S, boscalid, bromothalonil, bromuconazole, bupirimate, buthiobate, butylamine, calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1,1'-dioxide, dichlofluanid, diclomezine, dichlone, dicloran, dichlorophen, dichlozoline, diclobutrazol, diclocymet, diethofencarb, difenoconazole, difenzoquat, diflumetorim, O,O-di-iso-propyl-S-benzyl thiophosphate, dimefluazole, dimetachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)-N-benzyl-N ([methyl (methyl-thioethylideneamino-oxycarbonyl) amino] thio)-β-alaninate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexa chlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandipropamid, maneb, mebenil, mecarbinzid, mefenoxam, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-iso-propyl, nuarimol, octhilinone, ofurace, organomercury compounds, orysastrobin, osthol, oxadixyl, oxasulfuron, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-Al, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram and zoxamide.

In particular, the following fungicidal mixing partners are preferred:

a strobilurin fungicide selected from the group consisting of azoxystrobin, dimoxystrobin, fluoxastrobin, kresoxim-methyl, metominostrobin, orysastrobin, picoxystrobin, pyraclostrobin; trifloxystrobin;

an azole fungicide selected from the group consisting of azaconazole, bromuconazole, cyproconazole, difenoconazole, diniconazole, diniconazole-M, epoxiconazole, fenbuconazole, fluquinconazole, flusilazole, flutriafol, hexaconazole, imazalil, imibenconazole, ipconazole, metconazole, myclobutanil, oxpoconazole, pefurazoate, penconazole, prochloraz, propiconazole, prothioconazole, simeconazole, tebuconazole, tetraconazole, triadimefon, triadimenol, triflumizole, triticonazole, diclobutrazol, etaconazole, furconazole, furconazole-cis and quinconazole;

a morpholine fungicide selected from the group consisting of aldimorph, dodemorph, fenpropimorph, tridemorph, fenpropidin, spiroxamine and piperalin;

an anilino-pyrimidine fungicide selected from the group consisting of cyprodinil, mepanipyrim and pyrimethanil;

a fungicide selected from the group consisting of benalaxyl, benalaxyl-M, benomyl, bitertanol, boscalid, captan, carboxin, carpropamid, chlorothalonil, copper, cyazofamid, cymoxanil, diethofencarb, dithianon, famoxadone, fenamidone, fenhexamide, fenoxycarb, fenpiclonil, fluazinam, fludioxonil, flutolanil, folpet, guazatine, hymexazole, iprodione, lufenuron, mancozeb, metalaxyl, mefenoxam, metrafenone, nuarimol, paclobutrazol, pencycuron, penthiopyrad, procymidone, proquinazid, pyroquilon, quinoxyfen, silthiofam, sulfur, thiabendazole, thiram, triazoxide, tricyclazole, isopyrazam, sedaxane, fluxapyroxad, solatenol and 3-(difluoromethyl)-N-methoxy-1-methyl-N-[1-methyl-2-(2,4,6-trichlorophenyl)ethyl]pyrazole-4-carboxamide, Even more preferably, the polymorph of the invention is combined with a strobilurin or azole.

Whilst compositions comprising the polymorph of the invention and another fungicide are explicitly disclosed above, the skilled man will appreciate that the invention extends to three-way, and further multiple combinations comprising the above two-way mixtures.

For the avoidance of doubt, even if not explicitly stated above, the mixing partners of may also be in the form of any suitable agrochemically acceptable ester or salt, as mentioned e.g. in The Pesticide Manual, Thirteenth Edition, British Crop Protection Council, 2003.

The present invention will now be described by way of the following non-limiting examples and figures, wherein.

EXAMPLES

1. Preparation of Polymorphs—hydrate

A racemic mixture of the compound of formula (I) was prepared as described in WO 2008/131901 and then 0.5 g added to a 30% water/methanol solution (10 mL) at 25° C. to form a suspension. This suspension was stirred at room temperature for 5 days. The crystals were isolated by filtration under reduced pressure and air dried. Similar results were obtained by stirring a suspension of the crystals in 75% water/acetone for 5 days.

Crystals of the hydrate were also isolated by crystallisation from 20% water/acetonitrile. Crystals (0.5 g) were added to a 20% water/MeCN solution (10 mL) and heated (ca. 45° C.) to form a solution. This solution was then allowed to cool to room temperature. Crystal growth was observed over the following 48 hours. These resultant slurries were stirred for a further 48 hours at room temperature and the crystals isolated by filtration under reduced pressure and air dried.

2. Preparation of Polymorphs—anyhydrous Forms 1 and 2

A racemic mixture of the compound of formula (I) was prepared as described in WO 2008/131901. 0.1 g of this compound was combined with enough methanol to form an undersaturated solution (Form 1) or with enough acetonitrile to form an undersaturated solution (Form 2) at 25° C. The solvent was then allowed to evaporate to dryness slowly at room temperature.

3. Analysis of Polymorphs

After preparation by the methods detailed above, the samples were subject to analysis by powder X-ray diffraction and/or single crystal X-ray diffraction and/or differential scanning calorimetry (DSC).

Figure 1:
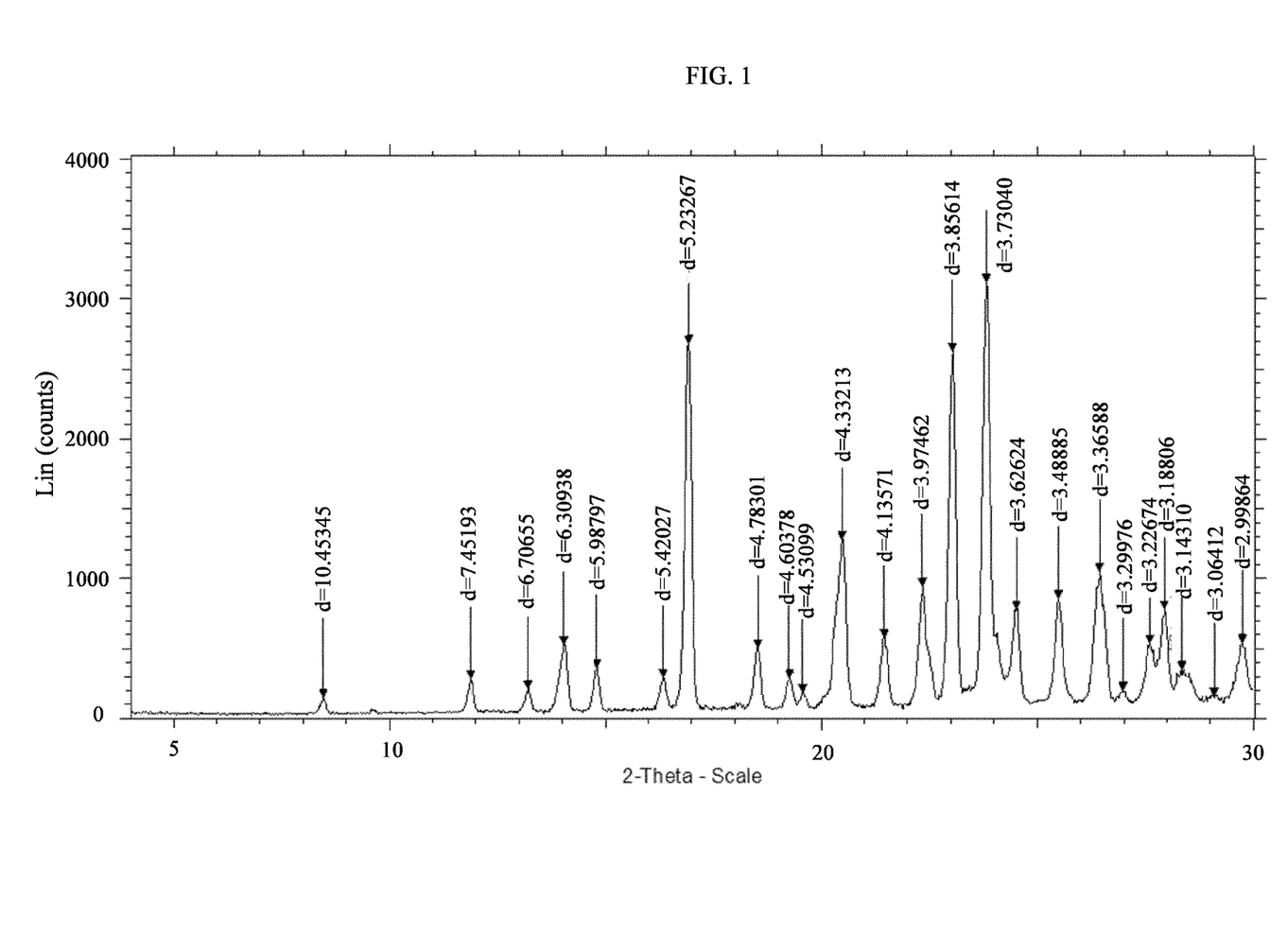
FIG. 1 shows the powder X-ray diffraction pattern of the hydrated crystalline polymorph of the invention.
Figure 5:
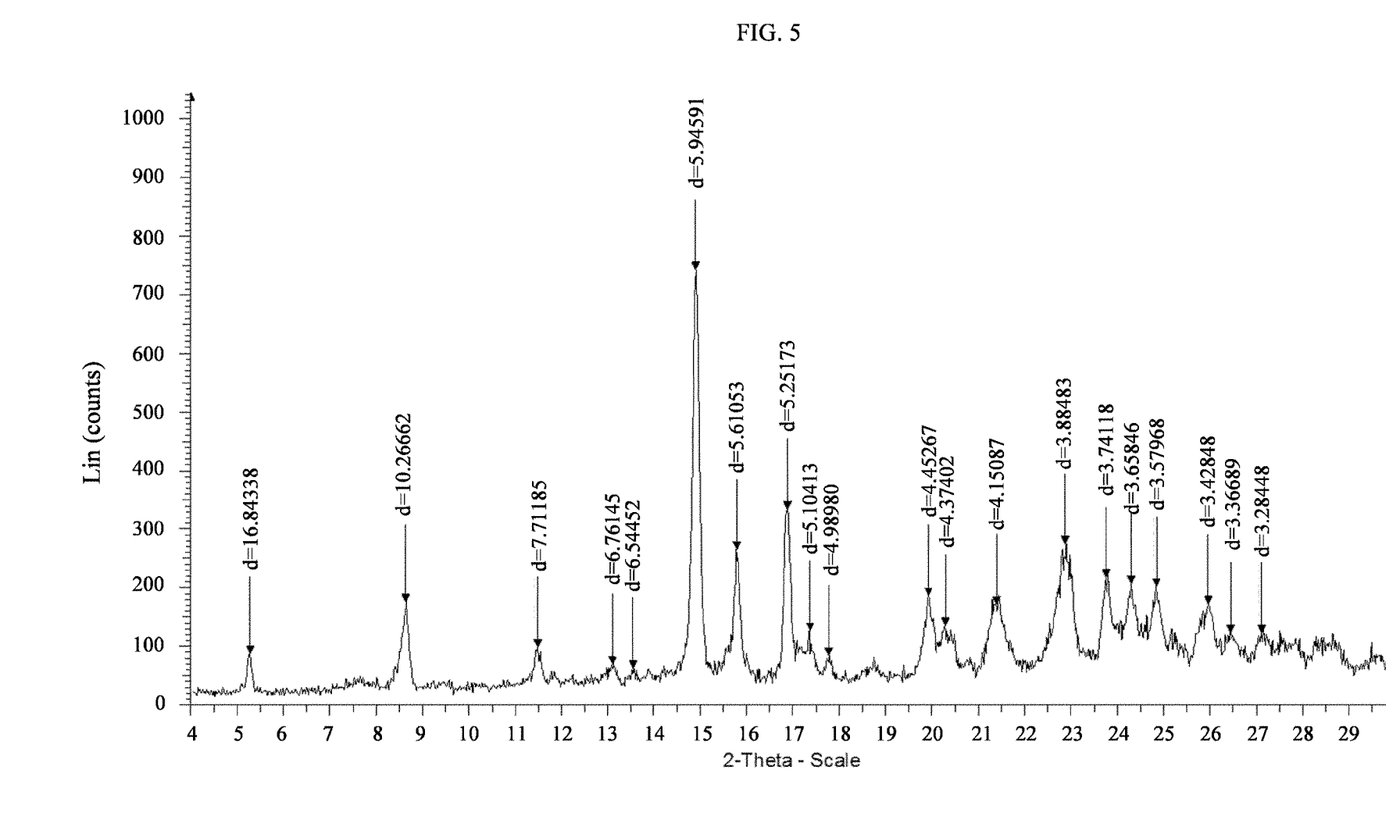
FIG. 5 shows the measured powder X-ray diffraction pattern of the anhydrous Form 2 polymorph.

Powder X-ray diffraction analysis of solid material was carried out using the Bruker D8 powder diffractometer at room temperature and at relative humidities above 40%. Samples were mounted in Perspex sample holders and the samples flattened. The sample holder was rotated and X-rays were collected from 4° to 34° 2-theta, with a scan time of 25 to 30 minutes depending on the pattern intensity. A PXRD trace of the hydrate is shown in FIG. 1 and of the anhydrous Form 2 in FIG. 5

Figure 4:
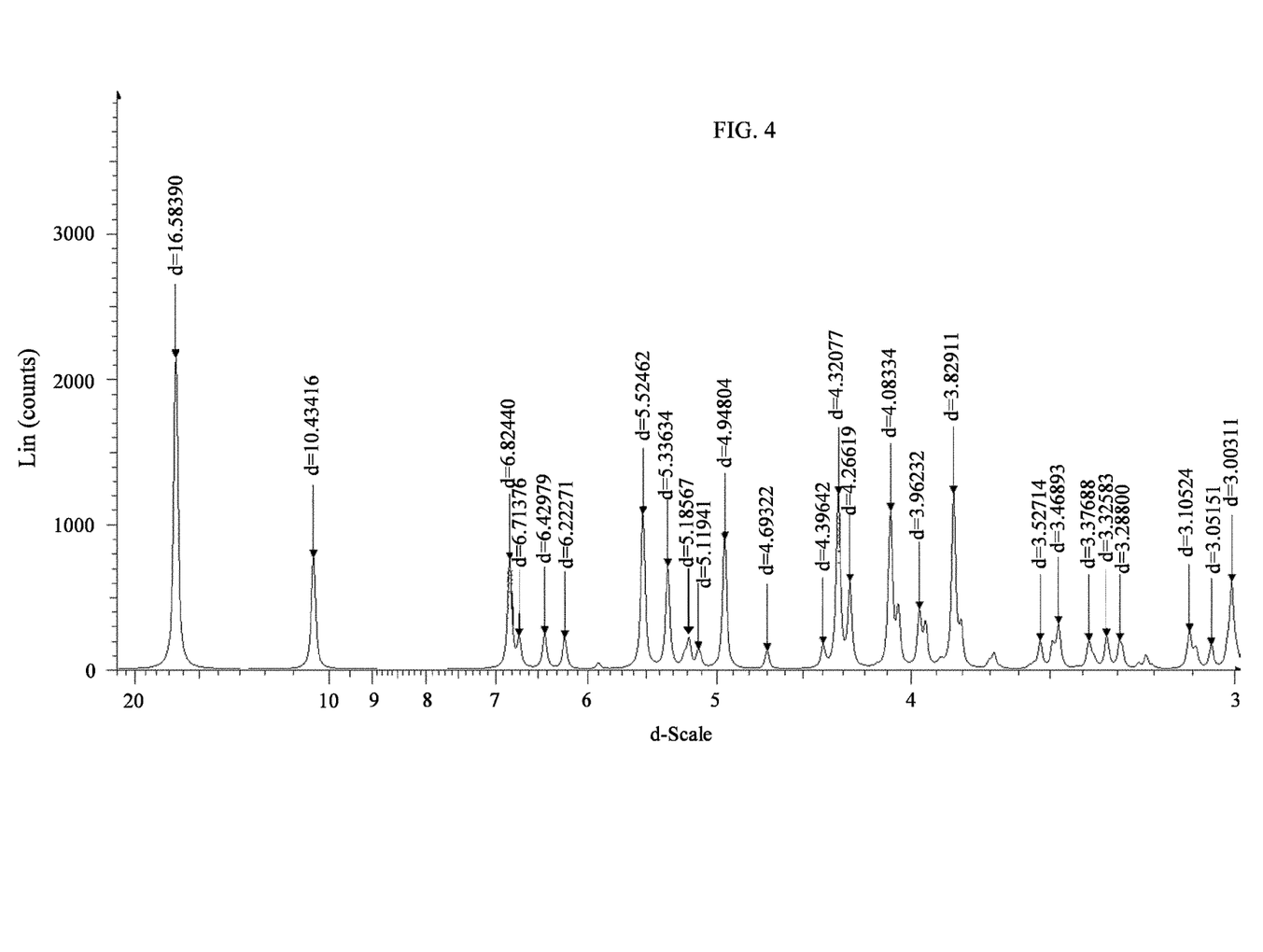
FIG. 4 shows the predicted powder X-ray diffraction pattern of the anhydrous Form 1 polymorph.

Single crystal intensity data was collected on an Oxford Xcalibar PX Ultra diffractometer using Cu Kα radiation (λ=1.5418 Å) with a graphite monochromator. The crystal was mounted in Paratone N oil at room temperature for data collection. The data was solved using the CRYSTALS software package. This data was used to produce a predicted powder X-ray diffraction pattern for the anhydrous Form 1, which is shown in FIG. 4.

DSC was carried out using a Mettler Toledo DSC 820 or DSC1. A sample loading of around 5 mg was used and this was heated from 40° C. to 250° C. at a rate of 10° C./minute on the DSC820 or from 25° C. to 250° C. at a rate of 10° C./minute on the DSC1. The lid of the DSC crucible was pierced to allow the escape of any gas formed during the heating of the sample.

Figure 2:
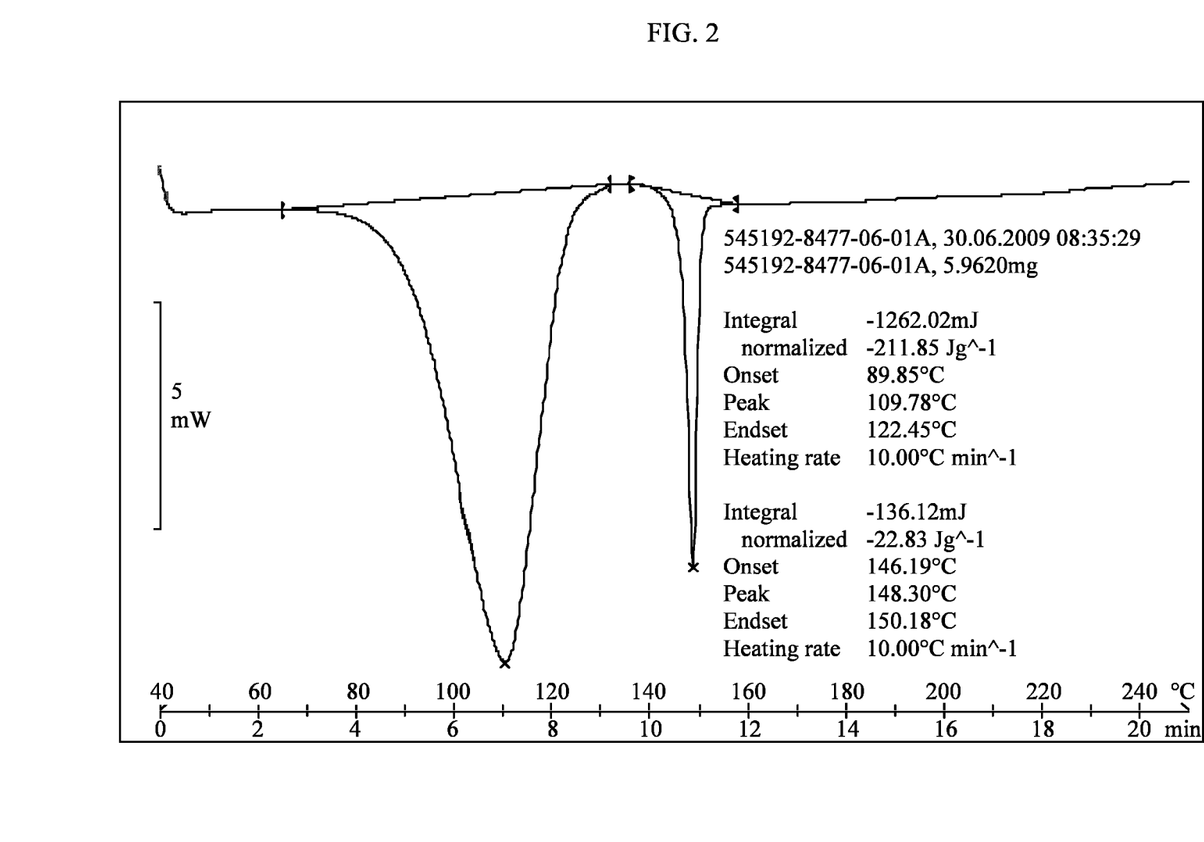
FIG. 2 shows a DSC trace of the hydrated crystalline polymorph of the invention.

The DSC analysis confirmed the presence of a hydrate with a dehydration/melting point between 80 and 125° C. and the two anhydrous forms with melting points of 149.2° C. and 147.4° C., respectively. A DSC trace of the hydrate is shown in FIG. 2.

4. Stability of Polymorphs

The thermodynamic stability of hydrated crystals depends not only on temperature but also on the abundance of water, or more precisely, the water activity ($a_w$), which is equivalent to the relative humidity. In order to determine under which conditions the anhydrous polymorph Form 1 and the hydrate are stable, a series of competitive slurries containing both crystal forms were prepared in different water/methanol mixtures and at a range of temperatures. The resulting crystals were analysed by DSC to determine the stable form under the given conditions. Table 3 shows the boundary between the two forms based on this DSC data.

TABLE 3

| Water in Methanol (%) | Temperature (° C.) | | | | | | | | | | | |
|---|---|---|---|---|---|---|---|---|---|---|---|---|
| | 5 | 10 | 15 | 20 | 25 | 30 | 35 | 40 | 45 | 50 | 55 | 60 |
| 35 | — | — | — | — | — | — | — | — | — | — | — | H |
| 30 | — | — | — | — | — | — | — | — | — | — | — | — |
| 25 | — | — | — | — | — | — | — | — | H | — | — | H |
| 20 | — | — | — | H | — | H | H | H | H | — | — | H |
| 15 | H | — | H | — | — | — | — | — | — | H | — | A |
| 12.5 | H | — | — | — | — | — | — | — | — | — | — | — |
| 10 | H | — | H | U | — | U | A | A | A | — | — | A |
| 7.5 | H | — | H | — | — | — | — | — | — | — | — | — |
| 5 | A | — | — | A | — | — | A | A | A | — | — | A |
| 1 | A | — | — | A | — | — | A | A | A | — | — | A |

Figure 3:
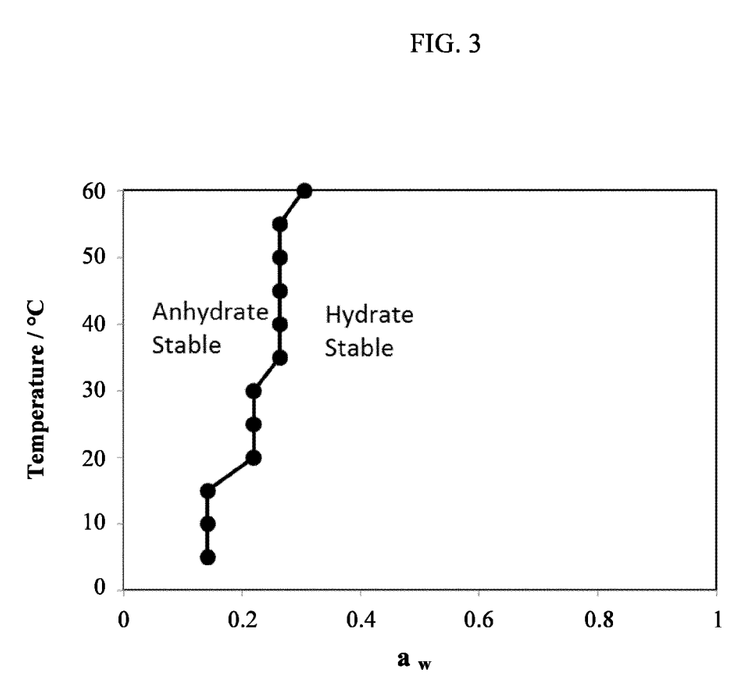
FIG. 3 shows a phase diagram showing the stability of the hydrated and anhydrous crystalline forms of the compound of formula (I).

Note:
A indicates the anhydrous form is the stable form
H indicates the hydrate is the stable form
U data was inconclusive
— indicates not tested From the data above, the water/methanol compositions were converted into water activities and a phase diagram was constructed. The phase diagram is shown in FIG. 3.

The phase diagram shows that temperatures in excess of 60° C. would be required to dehydrate the hydrate of compound (I) at normal ambient relative humidities. This indicates that the hydrate would be the stable form of compound (I) in suspension concentrate formulations and, in addition, would also be more stable in other, non-aqueous, formulations upon their dilution with water in the spray tank. Use of the anhydrous Form 1 under these conditions, would likely lead to polymorphic conversion to the hydrate and concomitant crystal growth potentially resulting in blocked nozzles in spray equipment.

5. Stability of Formulations of Polymorphs

Two standard suspension concentrate (SC) formulations were separately prepared using the anhydrous Form 1 polymorph and the hydrated polymorph. The SC of the anhydrous Form 1 was contaminated with 5% of the hydrated form and placed in a temperature cycling oven varying from 0° C. to 40° C. over 12 hours.

Figure 6:
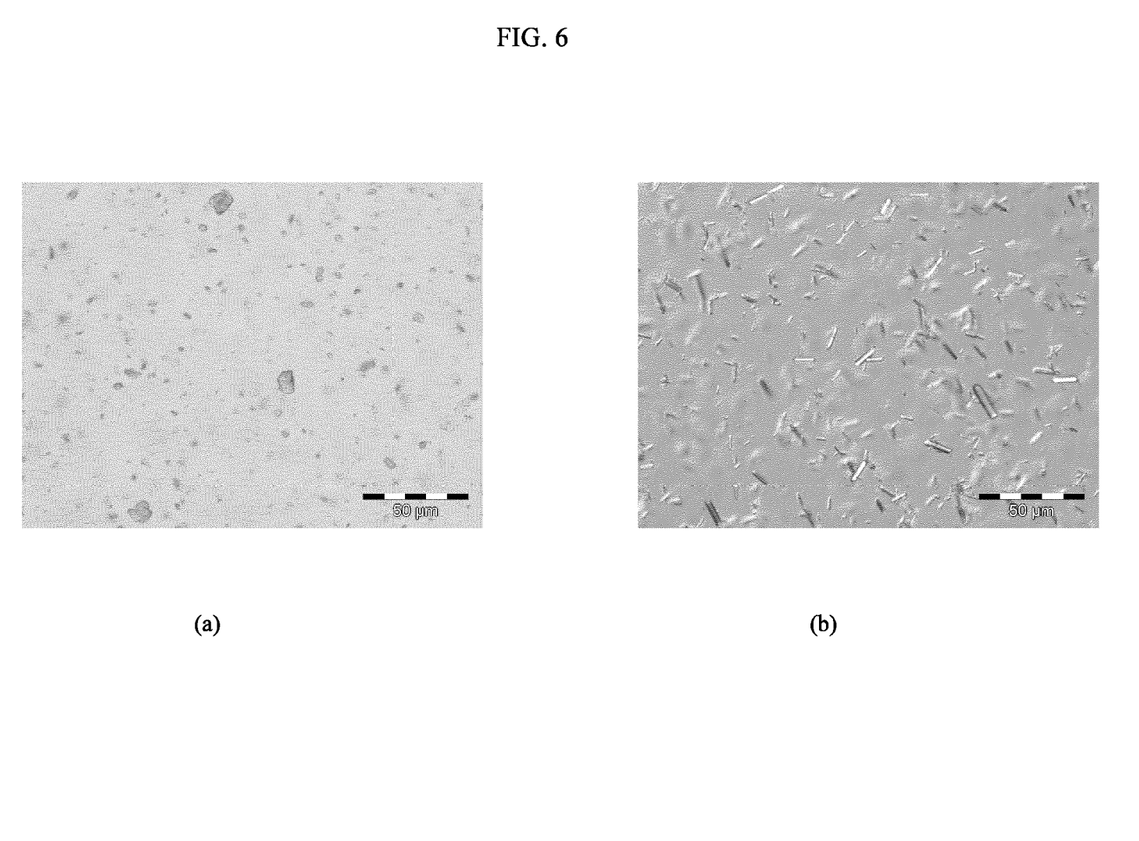
FIG. 6 shows micrographs of crystal growth in a formulation of the anhydrous Form 1 polymorph (a) before incubation with 5% of the hydrated form and (b) after 2 weeks incubation with the hydrated form.
Figure 7:
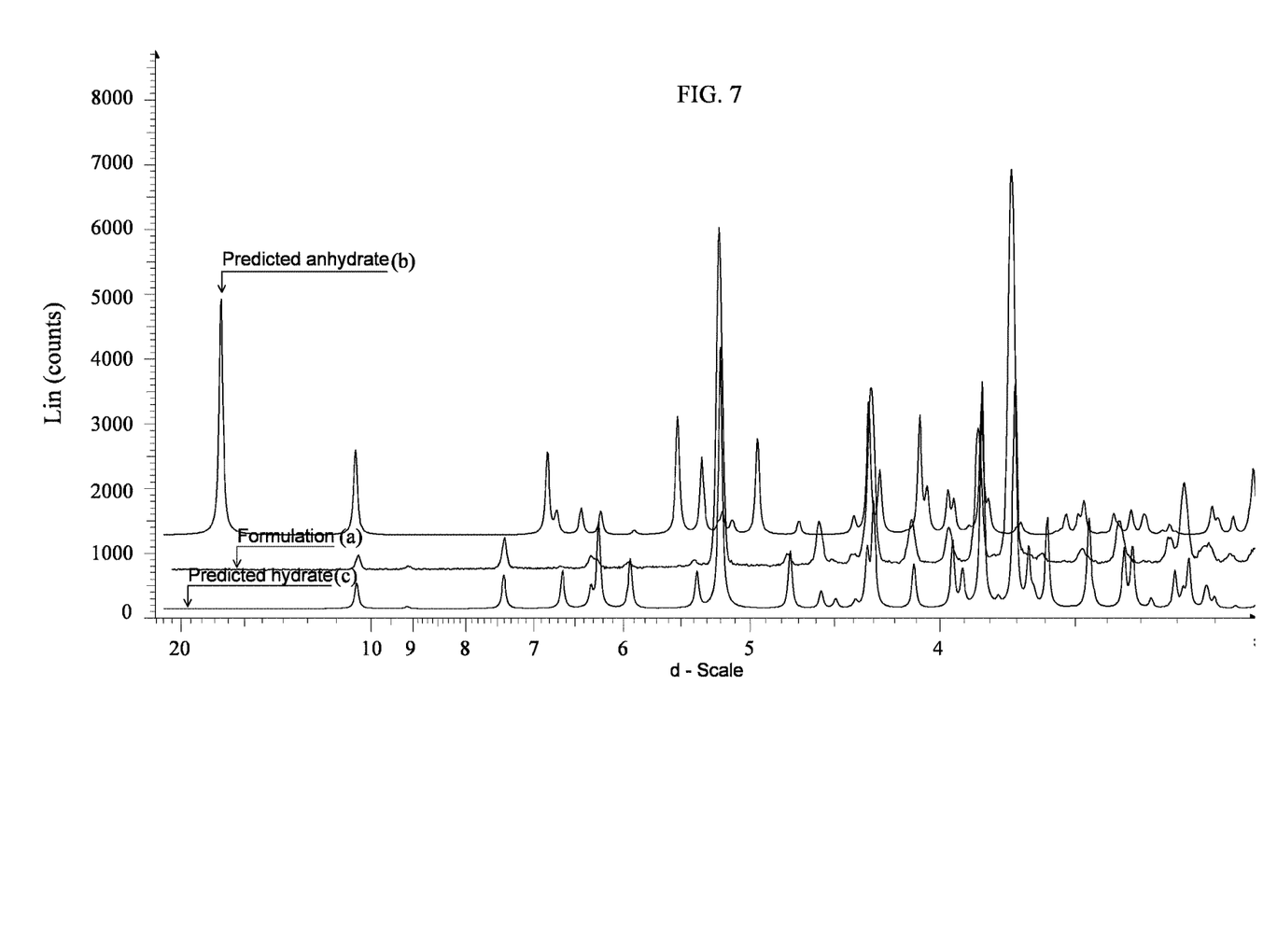
FIG. 7 shows the measured powder X-ray diffraction pattern of the formulation of Example 5 after two weeks (a) compared with predicted powder X-ray diffraction patterns of the anhydrous Form 1 polymorph (b) and the hydrated polymorph (c).

After two weeks, the sample was inspected. Microscopy showed that the size of the crystals had increased substantially. Micrographs of crystal size are shown in FIG. 6. Some crystals were removed from the formulation and dried. The powder X-ray diffraction pattern was collected—this showed that all of the anhydrous polymorph Form 1 had fully converted to the hydrated form. The comparative powder X-ray diffraction trace is shown in FIG. 7.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A hydrated crystalline polymorph of the compound of formula I which has a powder X-ray diffraction pattern comprising at least three d values selected from the group consisting of 10.45 ±0.2, 7.45±0.2, 6.71±0.2, 6.31±0.2, 5.99±0.2, 5.42±0.2, 5.23±0.2, 4.78±0.2, 4.60±0.2, 4.53±0.2, 4.33±0.2, 4.14±0.2, 3.97±0.2, 3.86±0.2, 3.73±0.2, 3.62±0.2, 3.49±0.2, 3.37±0.2, 3.30±0.2, 3.23±0.2, 3.19±0.2, 3.14±0.2, 3.06±0.2 and 3.00±0.2 and which has no peak in the powder X-ray diffraction pattern at d=16.58±0.2 and d =16.84±0.2.

2. The crystalline polymorph of claim 1, which has the following lattice parameters: a=18.28(5 ), b=12.65(5 ), c=7.81(5 ), α=90.00 , β=90.00 , Y=90.00 and volume=1805.0(5) Å$^3$ .

3. The crystalline polymorph of claim 1, which is a monohydrate containing 4.3 ±0.2% w/w water.

4. The crystalline polymorph of claim 1, which has a dehydration/melting point of between 80 and 125° C.

5. An agricultural composition comprising a polymorph as claimed in claim 1 and at least one agriculturally acceptable carrier or diluent.

6. The composition of claim 5, which comprises at least one further fungicide.

7. The composition of claim 6, wherein the further fungicide is a strobilurin or an azole.

8. A method of preventing or controlling fungal infection on plants or plant propagation material comprising treating the plant or plant propagation material with a fungicidally effective amount of an agricultural composition of claim 5.

* * * * *